(12) United States Patent
Valdez

(10) Patent No.: US 9,221,737 B2
(45) Date of Patent: Dec. 29, 2015

(54) PROCESS FOR THE OXIDATION OF CYCLOHEXANE

(75) Inventor: David Lee Valdez, Victoria, TX (US)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 14/415,161

(22) PCT Filed: Jul. 19, 2012

(86) PCT No.: PCT/US2012/047392
§ 371 (c)(1),
(2), (4) Date: Jan. 16, 2015

(87) PCT Pub. No.: WO2014/014464
PCT Pub. Date: Jan. 23, 2014

(65) Prior Publication Data
US 2015/0210619 A1     Jul. 30, 2015

(51) Int. Cl.
| | | |
|---|---|---|
| *C07C 45/33* | (2006.01) |
| *B01J 10/00* | (2006.01) |
| *C07C 29/50* | (2006.01) |
| *C07C 407/00* | (2006.01) |
| *B01J 19/00* | (2006.01) |

(52) U.S. Cl.
CPC ............ *C07C 45/33* (2013.01); *B01J 10/002* (2013.01); *B01J 19/006* (2013.01); *C07C 29/50* (2013.01); *C07C 407/00* (2013.01); *B01J 2219/00777* (2013.01); *C07C 2101/14* (2013.01)

(58) Field of Classification Search
CPC ........ C07C 45/33; C07C 29/50; C07C 407/00
USPC .................... 568/358, 360, 670, 836
See application file for complete search history.

(56) References Cited

U.S. PATENT DOCUMENTS

| | | | | |
|---|---|---|---|---|
| 3,530,185 | A | * | 9/1970 | Pugi .............................. 568/358 |
| 3,694,511 | A | * | 9/1972 | Nouvel ......................... 568/342 |
| 3,927,108 | A | * | 12/1975 | Van De Moesdijk et al. 568/342 |
| 3,957,876 | A | * | 5/1976 | Rapoport et al. ............. 568/358 |
| 3,987,100 | A | * | 10/1976 | Barnette et al. .............. 568/358 |
| 4,675,450 | A |   | 6/1987 | Lyon et al. |
| 5,780,683 | A | * | 7/1998 | Greene et al. ................ 568/358 |
| 6,703,529 | B1 | * | 3/2004 | Fodor et al. .................. 568/342 |
| 6,888,034 | B1 | * | 5/2005 | Landray et al. .............. 568/357 |

FOREIGN PATENT DOCUMENTS

WO    2014/014464 A1    1/2014

OTHER PUBLICATIONS

International Preliminary Report on Patentability received for PCT Patent Application No. PCT/US2012/047392, Completed on Nov. 11, 2014, 7 Pages.
International Search Report and Written Opinion received for PCT Patent Application No. PCT/US2012/047392, mailed on Apr. 10, 2013, 9 Pages.

* cited by examiner

*Primary Examiner* — Sikarl Witherspoon
(74) *Attorney, Agent, or Firm* — Robert B. Furr, Jr.; Jeff Freeman

(57) ABSTRACT

A reaction zone is provided zone comprising a series of oxygen clean up zones and a series of oxidation zones. A first stream is introduced to oxidation clean up zones comprising liquid cyclohexane. Next, the first stream is passed downwardly from the oxygen clean up zones to the oxidation zones, while cross-currently passing the oxygen containing gas upwardly from the oxidation zones to the oxygen clean up zones. During the reaction, the oxidation zones are maintained at a temperature range of about 145° C. to about 170° C. The product mixture is withdrawn from the oxidation zones that comprises cyclohexylhydroperoxide (CHHP), cyclohexanone and cyclohexanol. An oxidation off-gas comprising less than 3.0% by volume of unreacted oxygen is withdrawn from the oxygen clean up zones.

10 Claims, 2 Drawing Sheets

PROCESS FOR THE OXIDATION OF CYCLOHEXANE

FIELD OF THE INVENTION

This disclosure relates to a process for the air oxidation of cyclohexane. More specifically, it relates to a method for maintaining the oxygen content of the off-gas from the oxidation process.

BACKGROUND OF THE INVENTION

The air oxidation of cyclohexane is an important process for the production of caprolactam and adipic acid, which are used in the manufacture of synthetic products, such as nylon. The oxidation of cyclohexane by air produces a reaction product comprising cyclohexanol (A), cyclohexanone (K) cyclohexylhydroperoxide (CHHP) and small amounts of byproducts. Cyclohexanone (K) and cyclohexanol (A) are the main product of the overall process and the mixture is commonly known as KA oil. Several patents, herein incorporated by reference, such as U.S. Pat. Nos. 3,530,185, 3,987,100, 5,780,683, 6,888,034 and 6,703,529 teach the preparation of a mixture containing cyclohexanol, cyclohexanone and cyclohexylhydroperoxide by the air oxidation of cyclohexane.

It is well known that CHHP in a mixture containing cyclohexanol, cyclohexanone, other products of the air oxidation reactions will react to form KA oil. However, this process does not result in a high yield of KA oil and other waste materials are formed. It has been found that the highest yields of KA oil can be achieved when the oxidation of cylcohexane is performed under conditions that result in a greater amount of CHHP and the CHHP is then treated by hydrogenation in a separate process to cyclohexanone (K) and cyclohexanol (A) to give an increased overall yield of KA oil. For example, the preparation of cyclohexanol and cyclohexanone from cyclohexylhydroperoxide by hydrogenation has been in described in U.S. Pat. Nos. 3,694,511 and 3,927,108, herein incorporated by reference.

The air oxidation reaction is generally conducted at temperatures from about 130° C. to about 200° C. Various types of reactors can be implemented for commercial use and these include single autoclaves, multiple autoclaves in series, horizontal single reactors with multiple compartments, and multistage column reactors. Air is generally used as the primary source of oxygen. Any unreacted oxygen (along with the nitrogen present in the air) leaves the reactor or reactors as a gaseous effluent or off-gas. The off-gas also contains vaporized cyclohexane and other compounds. The amount of unreacted oxygen in the off-gas is commonly referred to as "oxygen leakage." The vaporized cyclohexane and other products in the off-gas are condensed and recovered, and the off-gases leave the system, usually to an abatement system. The oxidation products that are produced from the oxidation reaction are recovered from the liquid effluent from the reactor or reactors, and the unreacted cyclohexane is recycled.

It has been observed that at lower oxygen leakage levels from a reactor, the higher the formation of undesirable byproducts and hence the lower the yield to desirable oxidation products. In the oxidation of cyclohexane, the yield of cyclohexanone, cyclohexanol and CHHP, can be optimized by operating at high oxygen leakage (i.e. concentration of unreacted oxygen in the mixture of cyclohexane free oxygen, nitrogen and other gases and vapors). Unfortunately, at oxygen leakage concentration in excess of 8 vol %, unsafe flammable mixtures can form in the effluent gas stream. Therefore, as a margin of safety the oxygen leakage is usually kept below 4 vol %. Higher oxygen leakage also means that the air being fed to the reactor(s) is not being fully utilized. In other words, the process will requires more air, which leads to increased compression cost. In addition, an increased volume of off-gas causes increased cost for off-gas treatment.

U.S. Pat. No. 3,957,876 teaches a method to reduce oxygen leakage from a cyclohexane oxidation process through the use of oxygen clean up zones. The oxygen clean up zones allows additional consumption of oxygen by reacting it with cyclohexane and thus produces an off-gas that contains oxygen of adequately low concentration so that an explosion hazard can be avoided.

One disadvantage of the prior art is that it is difficult to maintain a desired range of oxygen leakage leaving the reactor, while maintaining the desired yield from the cyclohexane oxidation reaction. The examples in U.S. Pat. No. 3,957,876 teach an oxygen leakage ranging from 2% to 10% by volume.

It has been found that the temperature profile in the reactor is critical to acquiring a desired yield from the oxidation reaction and maintaining the level of oxygen leakage. The temperatures in the reaction section of the column must be maintained sufficiently high to sustain the oxidation reaction. However, excessively high temperatures are detrimental to yield because they will lead to an increased rate of oxidation of the KA and CHHP to undesired byproducts.

Therefore, there is a need for an improved process for the air oxidation of cyclohexane, wherein the temperature profile in the oxidation reactor is maintained in order to maximize the yield of desired oxidation products and control the oxygen leakage in the reactor off-gas.

SUMMARY OF THE INVENTION

The present invention relates to a process for the oxidation of cyclohexane wherein the temperature profile in the reaction zone is maintained to control the level of oxygen leakage leaving the process. The temperature profile in the reaction zone is maintained by controlling the distribution of oxygen containing gas at different areas of the reaction zone.

An embodiment of the present invention comprises the steps of;
a) providing a reaction zone comprising a series of oxygen clean up zones and a series of oxidation zones, wherein the oxygen clean up zones and the oxidation zones are in fluid communication;
b) introducing a first stream comprising liquid cyclohexane, and optionally a cyclohexane oxidation catalyst into the oxygen cleanup zones;
c) introducing an oxygen containing gas into the oxidation zones;
d) passing the first stream downwardly from the oxygen clean up zones to the oxidation zones, while cross-currently passing the oxygen containing gas upwardly from the oxidation zones to the oxygen clean up zones, wherein the reaction between the first stream and the oxygen containing gas produces a product mixture, and wherein the oxygen containing gas is distributed to the oxidation zones through a plurality of conduit banks, wherein each conduit bank feeds one or more oxidation zones and wherein a different flow rate of the oxygen containing gas can be maintained in each conduit bank;
e) maintaining the oxidation zones at a temperature range of about 145° C. to about 170° C.;
f) withdrawing a product mixture from the oxidation zones that comprises cyclohexylhydroperoxide (CHHP), cyclohexanone and cyclohexanol; and g) withdrawing from the oxygen clean up zones an oxidation off-gas comprising less than 3.0% by volume of unreacted oxygen.

In another embodiment, the reaction zone comprises a single reaction vessel.

In another embodiment, the oxidation off-gas withdrawn from the clean up zones comprises unreacted oxygen in the range from about 1.0% to about 2.0% by volume.

In another embodiment, the cyclohexane catalyst comprises soluble salts of at least one metal selected from the group consisting of cobalt and chromium.

In another embodiment, the cyclohexane catalyst is a soluble cobalt salt selected from a group comprising cobalt naphthenate, cobalt octoate, cobalt laurate, cobalt palminate, cobalt stearate, cobalt linoleate, cobalt acetylacetonate and mixtures thereof.

In another embodiment, the flow rate of the oxygen containing gas within each conduit bank is controlled to maintain the temperature of different areas of the reaction zone within a predetermined range.

In another embodiment, each conduit bank comprises of a plurality of gas conduits.

In another embodiment, each gas conduit comprises a gas sparger.

In another embodiment, the temperature of the product mixture exiting the oxidation zones is maintained a temperature in the range from about 145° C. to about 170° C.

In another embodiment, the temperature of the off-gas exiting the oxygen clean up zones is maintained a temperature in the range from about 110° C. to about 150° C.

DETAILED DESCRIPTION OF THE INVENTION

The present invention relates to a process for the oxidation of cyclohexane wherein the temperature profile in the reaction zone is maintained to control the level of oxygen leakage leaving the process.

All patents, patent applications, test procedures, priority documents, articles, publications, manuals, and other documents cited herein are fully incorporated by reference to the extent such disclosure is not inconsistent with this invention and for all jurisdictions in which such incorporation is permitted.

Figure 1:
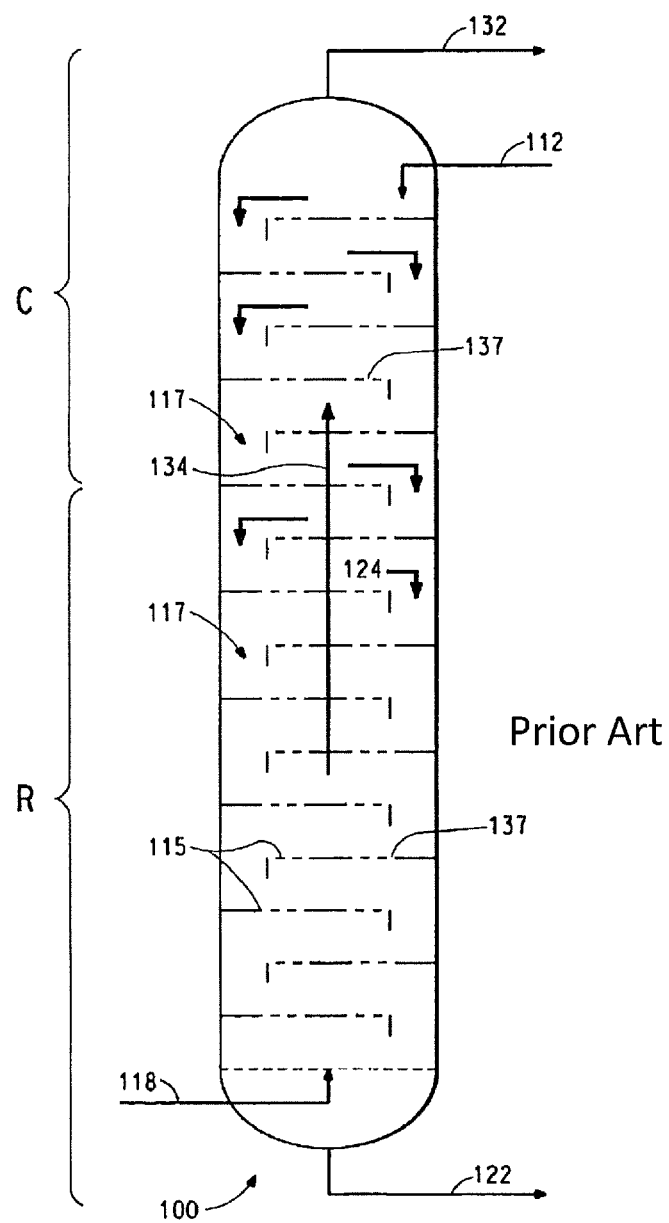
FIG. 1 is a process diagram depicting the prior art.

Referring now to FIG. 1, there is shown an apparatus 100 that illustrates the prior art as taught in U.S. Pat. No. 3,957,876, herein incorporated by reference. In apparatus 100, the top zone of the column indicated by a bracket identified as C is the oxygen clean-up zone and the bottom zone of the column indicated by a bracket identified as R is the oxidation zone. A stream of hot liquid cyclohexane 112 enters the top part of the oxygen clean-up reaction zone (C) and it flows across the trays 115 and downward through the down-comers 117. In doing so it contacts in a counter-current fashion a stream of gaseous effluent 134 coming from the oxidation zone (R) as in a normal tray column. The liquid effluent from the clean-up zone 124 comprising liquid cyclohexane, CHHP, Cyclohexanone and cyclohexanol enters the top part of the oxidation zone (R) and flows across the trays and downward through the down-corners of trays in the primary reaction zone, where it contacts an oxygen-containing gas in a counter-current fashion. The oxygen-containing gas 118 enters the bottom part of the primary reaction zone and flows upward through holes 137 in the trays 115 of the column. The primary source of heat input to the reaction zone is from the heat of reaction. Heat input to the system from the exothermic oxidation reaction varies directly with the amount of oxygen containing gas that is injected into the reaction zone.

In the description of the prior art above, the oxygen containing gas 118 enters the oxidation zone at a single or multiple points and is evenly distributed amongst the trays 115. This configuration does not allow the temperature in different areas of the column to be adjusted by the flow rate of the oxygen containing gas. As described herein, the current invention discloses a method of varying the flow rate of the oxygen containing gas at different areas of the reactor. This allows the temperature profile in different areas of the reactor to be varied to minimize the amount of cyclohexane feed needed and to control the range of oxygen leakage.

Figure 2:
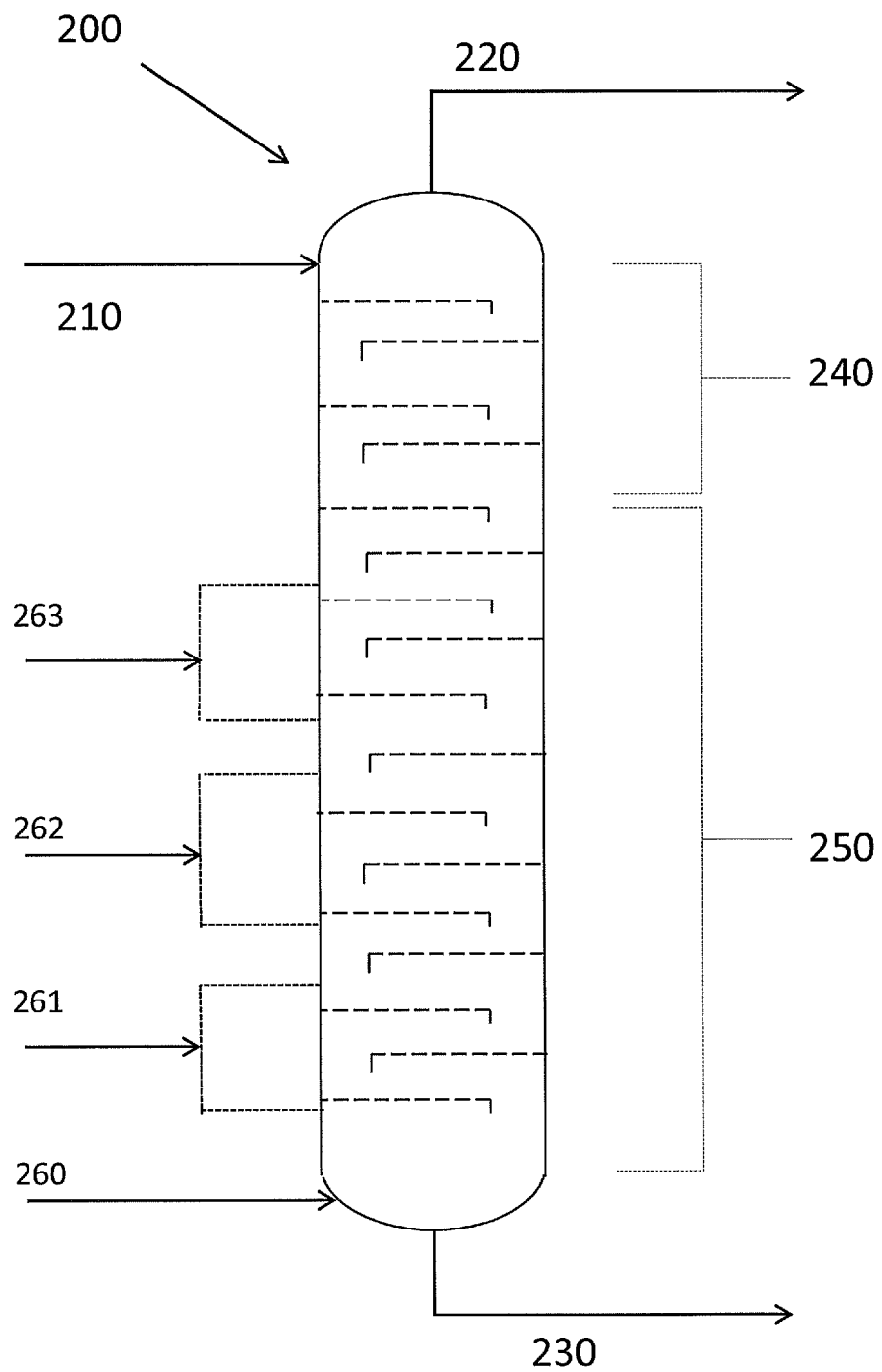
FIG. 2 is a process diagram depicting an embodiment of the present invention.

Referring now to FIG. 2, an exemplary embodiment of the present invention is will now be described. The cyclohexane oxidation reactor 200 comprises oxygen clean up zones 240 and oxidation zones 250, which are in fluid communication. The oxidation zones 250 may consist of a plurality of trays where the oxidation of cyclohexane can take place. The oxygen clean up zones 240 may consist of a plurality of trays where the heat from the oxidation reaction can be recovered. The oxidation zones and oxygen clean up zones may be contained in multiple vessels. In an exemplary embodiment of the current invention, the oxygen clean up zones 240 and the oxidation zones 250 are contained in a single reactor vessel 200.

The liquid cyclohexane in stream 210 may contain fresh cyclohexane and/or liquid cyclohexane recycled from any subsequent part of the process. Stream 210 is added at the top of the reactor 200 and travels cross-flow across the trays in oxidation clean up zones 240 and oxidation zones 250. A stream of cyclohexane oxidation catalyst (not shown) can optionally be added into the oxidation clean up zones. The catalyst may be any suitable cyclohexane catalyst known in the art, including soluble salts of cobalt or chromium, and mixtures thereof. If a cobalt catalyst is chosen, it may be selected from a group comprising cobalt naphthenate, cobalt octoate, cobalt laurate, cobalt palminate, cobalt stearate, cobalt linoleate, cobalt acetylacetonate and mixtures thereof.

The cyclohexane oxidation may also be carried out in the presence of a phosphoric ester, such as di(2-ethylhexyl)phosphoric acid. Such a process is disclosed in Lyon et al., U.S. Pat. No. 4,675,450, which disclosure is hereby incorporated by reference in the present application.

An oxygen containing gas is fed into the oxidation zones 250 through conduits banks 261, 262, 263 and stream 260. Stream 210 is fed downwardly from the oxygen clean up zones 240 to the oxidation zones 250, while countercurrently or cross-currently passing the oxygen containing gas upwardly from the oxidation zones 250 to the oxygen clean up zones 240, wherein the reaction between the first stream and the oxygen containing gas produces a product mixture 230. The product mixture 230 comprises cyclohexylhydroperoxide (CHHP), cyclohexanone and cyclohexanol and other oxidation products.

In an exemplary embodiment of the current invention, the oxygen containing gas is air. The oxygen containing gas is distributed to the oxidation zones through a plurality of conduit banks 261, 262 and 263, wherein each conduit bank feeds one or more oxidation zones 250 and wherein a different flow rate of the oxygen containing gas can be maintained in each conduit bank. In other embodiments of the invention, any number of conduits may be utilized. Additionally, air is also added to reactor 200 through bottom sparger 260. The flow rate of air in each conduit bank and bottom sparger 260 is independently set to maintain the temperature range in different areas of the reaction zone. Each conduit bank comprises of a plurality of gas conduits. The gas conduit may be gas spargers or other conduits that are commonly used in the industry. In an exemplary embodiment of the current invention, the flow rates of air through the conduit banks is adjusted to maintain the temperatures in the oxidation zones at a range of about 145° C. to about 170° C. The temperature of the product mixture 230 exiting the oxidation zones 250 is maintained a temperature in the range from about 145° C. to about 170° C.

Any unreacted oxygen (along with the nitrogen present in the air) leaves the oxidation clean up zones 240 as an off-gas stream 220. The off-gas 220 also contains vaporized cyclohexane and other compounds. The amount of unreacted oxygen in the off-gas is commonly referred to as "oxygen leakage." The vaporized cyclohexane and other products in the off-gas are condensed and recovered, and the off-gases leave the system, usually to an abatement system. The oxidation products that are produced from the oxidation reaction are recovered from the liquid effluent from the reactor or reactors, and the unreacted cyclohexane is recycled.

It is desirable to maintain an oxygen leakage level close to 2% without exceeding the safety limits. As the oxygen leakage increases and nears a value of 2% the air distribution is altered to inject more air in the lower conduit banks relative to upper conduit banks. As the temperature is lowered the reaction rate will decrease and oxygen leakage will increase. A lower reaction rate is desirable because it reduces the reaction of CHHP. In a free radical reaction environment, CHHP will react to KA oil at a lower yield than can be achieved in the hydrogenation reaction step downstream. It has been found that the highest yields of KA oil can be achieved when the oxidation of cylcohexane is performed under conditions that result in a greater amount of CHHP and the CHHP is then treated by hydrogenation in a separate process to give an increased overall yield of KA oil. Therefore, to achieve an optimum yield it is better to slow down the reaction of CHHP in the oxidation reactor. This can be achieved by running at lower temperatures. However, dropping the temperature too low can result in the oxygen leakage exceeding the allowable safety limits. As a result, a balance is maintained between yield and safe operating conditions by controlling the air flow distribution.

To maintain safe levels of oxygen leakage, the temperature of the off-gas 220 exiting the oxygen clean up zones 240 is maintained a temperature in the range from about 110° C. to about 150° C. In an exemplary embodiment of the current invention, the oxygen leakage in the off gas is maintained at less than 3.0% by volume of unreacted oxygen, measured on a VOC-free basis. More preferably, oxygen leakage is maintained in a range from about 1.0% to about 2.0% by volume, measured on a VOC-free basis.

EXAMPLES

The following Examples demonstrate the present invention and its capability for use. The invention is capable of other and different embodiments, and its several details are capable of modifications in various apparent respects, without departing from the scope and spirit of the present invention. Accordingly, the Examples are to be regarded as illustrative in nature and non-limiting.

Example 1

The following example illustrates the method of the current invention as used at INVISTA's Victoria cyclohexane oxidation process. The flow rate through the conduit banks are adjusted based on the oxygen leakage as measured in the off gas 220. As the oxygen leakage decreases, indicating a relatively higher conversion in the column, the air distribution is altered to inject less in the lower conduit banks relative the flow in the upper conduit banks.

The primary source of heat input to the column is from the heat of reaction. Heat input to the system from the exothermic oxidation reaction varies directly with the amount of air that is injected into the reactor. In addition, the air distribution in the column will affect the temperature profile and hot spots. Putting more air in the lower conduit bank versus a higher conduit bank will result in the bottom section of the reactor running hotter. Table 1 below is an example of the flow rate distribution used in the Victoria plant.

TABLE 1

| Conduit Bank Location | % of overall Air Flow Rate |
|---|---|
| Upper Conduit Bank | 15% |
| Middle Conduit Bank | 30% |
| Lower Conduit Bank | 37% |
| Base Sparger | 25% |

The reaction zone in the Victoria plant contains 17 trays, which include the oxidation zones (base and trays 1-13) and oxidation clean up zones (trays 14-17). The temperatures of the materials in the column are measured on trays 2, 5, 8, 11, 14 and 17, as well as in the column base, tails line, and off-gas. Using the air flow distribution in Table 1, the temperature in the oxidation zones (base, and trays 1-13) has been observed between 145° C. and 170° C. The temperature in the base section (tails line) is 145-170° C. The temperature in the reactor off-gas temperature normally operates between 110-150° C.

Table 2 below shows oxygen leakage rates that were observed in the plant. As shown, the air flow distribution was maintained to keep the oxygen leakage in the desired range and close to the desired upper limit of that range to maximise yield while maintaining the safety margin.

TABLE 2

| Monthly Averages | Oxygen Leakage (%) |
|---|---|
| Month 1 | 1.99 |
| Month 2 | 1.98 |
| Month 3 | 1.99 |

Example 2

The following example is a method for the oxidation of cyclohexane. A reaction zone is provided zone comprising a series of oxygen clean up zones and a series of oxidation zones, wherein the oxygen clean up zones and the oxidation zones are in fluid communication. A first stream is introduced to oxidation clean up zones comprising liquid cyclohexane, and optionally a cyclohexane oxidation catalyst. In addition, an oxygen containing gas is introduced into the oxidation zones. Next, the first stream is passed downwardly from the oxygen clean up zones to the oxidation zones, while countercurrently or cross-currently passing the oxygen containing gas upwardly from the oxidation zones to the oxygen clean up zones, wherein the reaction between the first stream and the oxygen containing gas produces a product mixture. During the reaction, the oxidation zones are maintained at a temperature range of about 145° C. to about 170° C. The product mixture is withdrawn from the oxidation zones that comprises cyclohexylhydroperoxide (CHHP), cyclohexanone and cyclohexanol. An oxidation off-gas comprising less than 3.0% by volume of unreacted oxygen is withdrawn from the oxygen clean up zones.

Example 3

The process of Example 2 is repeated with additional steps. In this example, the reaction zone comprises a single reaction vessel.

Example 4

The process of Example 3 is repeated with additional steps. In this example, the oxidation off-gas withdrawn from the clean up zones comprises unreacted oxygen in the range from about 1.0% to about 2.0% by volume.

Example 5

The process of Example 4 is repeated with additional steps. In this example, the cyclohexane catalyst comprises soluble salts of at least one metal selected from the group consisting of cobalt and chromium.

Example 6

The process of Example 5 is repeated with additional steps. In this example, the cyclohexane catalyst is a soluble cobalt salt selected from a group comprising cobalt naphthenate, cobalt octoate, cobalt laurate, cobalt palminate, cobalt stearate, cobalt linoleate, cobalt acetylacetonate and mixtures thereof.

Example 7

The process of Example 6 is repeated with additional steps. In this example, wherein the oxygen containing gas is distributed to the oxidation zones through a plurality of conduit banks, wherein each conduit bank feeds one or more oxidation zones and wherein a different flow rate of the oxygen containing gas can be maintained in each conduit bank.

Example 8

The process of Example 7 is repeated with additional steps. In this example, the flow rate of the oxygen containing gas within each conduit bank is controlled to maintain the temperature of different areas of the reaction zone within a predetermined range.

Example 9

The process of Example 8 is repeated with additional steps. In this example, each conduit bank comprises of a plurality of gas conduits.

Example 10

The process of Example 9 is repeated with additional steps. In this example, each gas conduit comprises a gas sparger.

Example 11

The process of Example 10 is repeated with additional steps. In this example, the temperature of the product mixture exiting the oxidation zones is maintained a temperature in the range from about 145° C. to about 170° C.

Example 12

The process of Example 11 is repeated with additional steps. In this example, the temperature of the off-gas exiting the oxygen clean up zones is maintained a temperature in the range from about 110° C. to about 150° C.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

While the illustrative embodiments of the invention have been described with particularity, it will be understood that the invention is capable of other and different embodiments and that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the invention pertains.

What is claimed:

1. A process for the oxidation of cyclohexane comprising the following steps:
   a) providing a reaction zone comprising a plurality of oxygen clean up zones and a plurality of oxidation zones, wherein the oxygen clean up zones and the oxidation zones are in fluid communication;
   b) introducing a first stream comprising liquid cyclohexane into the oxygen cleanup zones;
   c) introducing an oxygen containing gas into the oxidation zones;
   d) passing the first stream downwardly from the oxygen clean up zones to the oxidation zones, while cross-currently passing the oxygen containing gas upwardly from the oxidation zones to the oxygen clean up zones, wherein the reaction between the first stream and the oxygen containing gas produces a product mixture, and wherein the oxygen containing gas is distributed to the oxidation zones through a plurality of conduit banks, wherein each conduit bank feeds one or more oxidation zones and wherein a different flow rate of the oxygen containing gas can be maintained in each conduit bank, and wherein the flow rate of the oxygen containing gas within each conduit bank is independently controlled to maintain the temperature of different areas of the reaction zone within a predetermined range;
   e) maintaining the oxidation zones at a temperature range of about 145° C. to about 170° C.;

f) withdrawing a product mixture from the oxidation zones that comprises cyclohexyihydroperoxide (CHHP), cyclohexanone and cyclohexanol; and g) withdrawing from the oxygen clean up zones an oxidation off-gas comprising less than 3.0% by volume of unreacted oxygen.

2. The process of claim 1 wherein the reaction zone comprises a single reaction vessel.

3. The process of claim 1 wherein the oxidation off-gas withdrawn from the clean up zones comprises unreacted oxygen in the range from about 1.0% to about 2.0% by volume.

4. The process of claim 1 wherein the reaction between the first stream and the oxygen containing gas takes place in the presence of a cyclohexane oxidation catalyst.

5. The process of claim 4 wherein the cyclohexane catalyst comprises soluble salts of at least one metal selected from the group comprising of cobalt and chromium.

6. The process of claim 4 wherein the cyclohexane catalyst is a soluble cobalt salt selected from a group comprising cobalt naphthenate, cobalt octoate, cobalt laurate, cobalt palminate, cobalt stearate, cobalt linoleate, cobalt acetylacetonate and mixtures thereof.

7. The process of claim 1 wherein each conduit bank comprises of a plurality of gas conduits.

8. The process of claim 1 wherein each gas conduit comprises a gas sparger.

9. The process of claim 1 wherein the temperature of the product mixture exiting the oxidation zones is maintained a temperature in the range from about 145° C. to about 170° C.

10. The process of claim 1 wherein the temperature of the off-gas exiting the oxygen clean up zones is maintained a temperature in the range from about 110° C. to about 150° C.

\* \* \* \* \*